US006555129B1

(12) United States Patent
Arth et al.

(10) Patent No.: US 6,555,129 B1
(45) Date of Patent: Apr. 29, 2003

(54) TRANSDERMAL THERAPEUTIC SYSTEM (TTS) CONTAINING OXYBUTYNIN

(75) Inventors: Christoph Arth, Dusseldorf (DE); Andreas Kollmeyer-Seeger, Langenfeld (DE); Stephan Rimpler, Hilden (DE); Hans-Michael Wolff, Monheim (DE)

(73) Assignee: Schwarz Pharma AG, Monheim (DE)

( * ) Notice: Subject to any disclaimer, the term of this patent is extended or adjusted under 35 U.S.C. 154(b) by 0 days.

(21) Appl. No.: 09/622,848

(22) PCT Filed: Mar. 16, 1999

(86) PCT No.: PCT/EP99/01707

§ 371 (c)(1),
(2), (4) Date: Oct. 26, 2000

(87) PCT Pub. No.: WO99/48493

PCT Pub. Date: Sep. 30, 1999

(30) Foreign Application Priority Data

Mar. 20, 1998 (DE) .......................................... 198 12 413

(51) Int. Cl.[7] ............................ A61L 15/16; A61K 9/14; A61F 15/00
(52) U.S. Cl. ....................... 424/448; 424/484; 424/487; 424/449; 424/443
(58) Field of Search ................................ 424/448, 449, 424/443

(56) References Cited

U.S. PATENT DOCUMENTS

| | | | |
|---|---|---|---|
| 5,730,999 A | * | 3/1998 | Lehmann et al. |
| 6,063,399 A | * | 5/2000 | Assmus et al. |
| 6,139,868 A | * | 10/2000 | Hoffmann |
| 6,165,499 A | * | 12/2000 | Kleinsorgen et al. |

FOREIGN PATENT DOCUMENTS

| | | | |
|---|---|---|---|
| DE | 43 10 012 A1 | 3/1993 | ........... A61L/15/44 |
| JP | 4266821 | 9/1992 | ......... A61K/31/135 |
| WO | WO 95/09007 | 4/1995 | ........... A61K/47/14 |
| WO | WO 96/33678 | 10/1996 | ........... A61F/13/00 |

\* cited by examiner

*Primary Examiner*—Carlos Azpuru
*Assistant Examiner*—Isis Ghali
(74) *Attorney, Agent, or Firm*—Marshall, Gerstein & Borun

(57) ABSTRACT

A transdermal therapeutic system (TTS) for transcutaneous administration of oxybutynin over a period of several days, in addition to a method for the production of the TTS without the use of solvents, are disclosed. The TTS contains a matrix mass containing oxybutynin in the form of a self-adhesive layer. The matrix mass includes ammonium-group-containing (meth)acrylic polymers, at least one citric acid ester, and 5–25 wt. % oxybutynin.

12 Claims, 1 Drawing Sheet

TRANSDERMAL THERAPEUTIC SYSTEM (TTS) CONTAINING OXYBUTYNIN

DESCRIPTION

The present invention concerns a Transdernal Therapeutic System (TTS) for the transcutaneous administration of oxybutynin over several days, as well as a method for its production without the use of solvents.

The bioavailability of orally or intravenously administered active ingredients is frequently unsatisfactory. Metabolization of many active ingredients in the liver can lead during the first passage through the liver to undesirable concentration relationships, toxic by-products and to the reduction of the activity and even to loss of activity. In comparison to oral administration, transdermal administration of active ingredients has various advantages. The introduction of the active ingredient can be controlled better over a longer period of time as a result of which high fluctuations in blood level are avoided. In addition, the required therapeutically effective dose can mostly be reduced significantly. In addition, patients frequently prefer a plaster to tablets, which must be taken once or several times daily.

In the past, in order to overcome the disadvantages of nontransdermal administration of active ingredients mentioned above, a number of transdermal therapeutic systems (TTS) with different structure were proposed for various active ingredients for the therapy of different diseases.

Thus, the technical documents given below describe a broad variety of systemically or locally reacting active ingredients, the parenteral administration of which is either based on dose-controlled or generally releasing systems.

For example, these are: U.S. Pat. Nos. 3,598,122 A; 3,598,123 A; 3,731,683 A; 3,797,494 A; 4,031,894 A; 4,201,211 A; 4,286,592 A; 4,314,557 A; 4,379,454 A; 4,435,180 A; 4,559,222 A; 4,568,343 A; 4,573,995 A; 4,588,580 A; 4,645,502 A; 4,702,282 A; 4,788,062 A; 4,816,258 A; 4,849,226 A; 4,908,027 A; 4,943,435 A and 5,004,610 A.

In the late sixties of this century, it was assumed originally theoretically that all active ingredients with short half-life but high activity and good penetration through the skin would be suitable for safe and effective administration via a TTS. These early expectations regarding the possibilities of transdermal administration of active ingredients by TTS could, however, not be fulfilled. The reason for this is mainly that the skin is equipped naturally with an inassessable variety of properties in order to maintain its function as an intact barrier to the penetration of substances that are foreign to the body. (See in this regard: Transdermal Drug Delivery: Problems and Possibilities, B. M. Knepp et al., CRC Critical Review and Therapeutic Drug Carrier Systems, Vol. 4, Issue 1 (1987).)

Therefore, transdermal administration is available only for those few active ingredients which have a suitable combination of many favorable characteristics. However, for a given active ingredient, these required characteristics that would permit safe and effective transdermal administration, cannot be predicted.

The requirements for an active ingredient suitable for transdermal administration are the following:

permeability through the skin,
no adverse influence on the adhesiveness of the plaster by the active ingredient,
avoidance of skin irritations,
avoidance of allergic reactions,
favorable pharmacokinetic properties,
favorable pharmacodynamic properties,
relatively broad therapeutic window,
metabolic properties which are consistent with therapeutic application with continuous administration.

Undoubtedly, the above list of requirements is not exhaustive. In order to have an active ingredient available for transdermal application, the "correct" combination of all these requirements is desirable.

What was said above for the active ingredient applies similarly to the TTS composition containing the particular ingredient and to its structure.

Usually, transdermal therapeutic systems (TTS) are plasters which are equipped with an impermeable cover layer, a removable protective layer and a matrix which contains the active ingredient or a reservoir with semipermeable membrane, which contains the active ingredient. In the first case, they are called matrix plasters and, in the second case, they are called membrane systems.

For the cover layer, usually polyesters, polypropylene, polyethylene, polyurethane, etc., are used which can also be metallized or pigmented. For the removable protective layer, among others, polyesters, polypropylene or even paper with silicone and/or polyethylene coating come into consideration.

For the active-ingredient-containing matrices which are usually used pharmaceutically or medically, materials based on polyacrylate, silicone, polyisobutylene, butyl rubber, styrene/butadiene copolymer or styrene/isoprene copolymer are used.

The membranes used in the membrane systems can be microporous or semipermeable and are usually based on an inert polymer, especially polypropylene, polyvinyl acetate or silicone.

While the active-ingredient matrix compositions can be self-adhesive, depending on the active ingredient used, one can also have active-ingredient containing matrices, which are not self-adhesive, so that, as a consequence of this, the plaster or TTS must have an overtape in its structure.

In order to ensure the required flux rate of the active ingredient, frequently skin penetration enhancers are necessary as additives, such as aliphatic, cycloaliphatic and/or aromatic-aliphatic alcohols, which can be monovalent or polyvalent and may have up to 8 C-atoms, including an alcohol/water mixture, a saturated and/or unsaturated fatty alcohol with 8 to 18 carbon atoms, a saturated and/or unsaturated fatty acid with 8 to 18 carbon atoms and/or their esters, as well as vitamins.

Furthermore, frequently stabilizers such as polyvinylpyrrolidone, α-tocopherol succinate, propyl gallate, methionine, cysteine and/or cysteine hydrochloride are added to the active-ingredient-containing matrix.

As the above discussion shows, numerous TTS structures and materials used for them are known. In any case, there are many interacting requirements to be considered when a drug is to satisfy a medical requirement in the form of a TTS.

The following problems are to be considered fundamentally in the development of active-ingredient-containing TTS:

1. The permeability of the active ingredient through the skin is too low in order to obtain the therapeutically necessary penetration rate and/or the lag-time until the therapeutically required plasma level is reached is too long, with the consequence that skin penetration enhancer additives must be administered.
2. The polymer matrix which is loaded with the active ingredient and optionally additionally with skin penetration enhancers is not stable physically upon long storage. Especially, recrystallization of the active ingredient may occur, which leads to an uncontrollable decrease of the active-ingredient release capacity of the TTS.
3. High load of the polymer carrier with active ingredient and/or skin penetration enhancers makes the adjustment of optimum adhesive properties of the transdermal system difficult in the case of self-adhesive polymer films.
4. The resorption rate of the active ingredient decreases during application over several days in an unacceptable manner, so that additional control layers and/or control components are necessary.
5. If the active-ingredient-loaded layers are made from organic solutions, the problem arises that solvent residues remain in the active-ingredient-containing layer after the drying process. Additionally, there is a danger of undesirable evaporation of volatile additives during manufacture. Since, for reasons of physical stability and skin compatibility of the system, as a rule, an attempt must be made to have a system completely free from solvent, the reservoir therefore must be built up in several layers, as the case may be. This again leads to an increase of manufacturing costs.
6. Furthermore, it is known from the literature that the fatty acid esters of polyvalent alcohols, which are frequently used to enhance penetration through the skin, have variable quality and contain impure diluents. This leads to poorly reproducible penetration increases (Burkoth et al., 1996, DE 196 22 902 A1).

Therefore, the problems described above require a large number of embodiments of Transdermal Therapeutic Systems, which are reflected in the state of the art in this field.

A more recent review on this is given, for example, in U.S. Pat. No. 5,662,926 A (Wick et al., 1997). This document describes transdermal systems which contain a monolithic thermo-plastic polymer film in which an active ingredient, preferably nicotine, is distributed homogeneously, as well as a method for solvent-free production of this active-ingredient-containing layer by mixing the active ingredient with the polymeric carrier material in the polymer melt, at temperatures from 170° C. to 200° C. In order to attach the active-ingredient-containing matrix film on the skin, there is an additional contact adhesive film which is applied onto the active ingredient matrix, and, if necessary, there is an additional plaster which has a larger area, and which is applied onto the active-ingredient-containing polymer film on the side of the matrix which is away from the skin.

Similar structural principles for transdermal systems of active-ingredient plasters are also described in WO 93/23025 A1 and WO 95/09007 A1 for oxybutynin-containing plaster preparations. According to WO 95/09007 A1, the skin penetration of oxybutynin from polymer matrices can be increased by monoglycerides in a mixture with lactic acid esters, and these penetration enhancer mixtures presumably do not cause any skin irritation or only a slight one.

The ethylene/vinyl acetate (EVA) copolymers, described in the above PCT documents as being used as active-ingredient carriers, are dissolved in a suitable organic solvent or are melted by heating in order to incorporate the oxybutynin. The films are then produced by coating and removing the solvent or by calendering of the homogeneous polymer/active-ingredient/enhancer mixture.

For incontinence treatment, according to WO 93/23025 A1, an oxybutynin plasma level of the order of 0.5–2 ng/mL is aimed at, corresponding to a release rate of 40–200 µg/h, preferably 80–160 µg/h.

According to U.S. Pat. No. 5,601,839 A, these permeation rates can be reached even with self-adhesive monolithic systems by the use of triacetin as penetration enhancer.

In the development of transdermal systems, polymers based on acrylic acid esters and methacrylic acid esters are of special interest because of their relatively good ability to take up and release a number of active ingredients. In order to avoid the use of solvents in the manufacture of matrix systems based on poly(meth)acrylate, DE 4310012 A1 describes a dermal therapeutic system in which one or several layers are made of mixtures of poly(meth)acrylates and are produced from the melt, and the first mixing component consists of (meth)acrylate polymers which contain functional groups, the second mixing component controls the flow behavior and contains only insignificant amounts of functional groups. The composite systems with poly(meth)acrylates with functional groups are supposed to make it possible to have controlled release of the active ingredient(s) on or through the skin and facilitate simple manufacture. Furthermore, the active-ingredient-containing formulations obtained by combination with poly(meth)acrylates with low glass temperature have the properties of a pressure-sensitive skin adhesive. However, while there are advantages in the manufacture in comparison to solvent-based methods, according to experience, these systems exhibit a number of disadvantages and these are caused by the following:
1. Longer thermal exposure of all TTS components during (1) manufacture of the polymer melt, (2) homogeneous incorporation of the active ingredient or ingredients and/or (3) coating of the hot active-ingredient-containing mass onto suitable carrier materials, with an increased risk of degradation or decomposition reactions in the polymer melt and/or during storage of the active-ingredient-containing polymer films.
2. Difficulties in the optimization of the cohesion/adhesion balance of the poly(meth)acrylate-containing layer for application for several days, since crosslinking of the acrylate copolymer with covalent bonds during manufacture of the active-ingredient-containing polymer matrix in the melt is not possible, in combination with problems that can arise because of cold flow of the polymer mass during application on the skin and/or during storage.

DE 196 53 606 A1 describes an adhesive and binder for TTS from well-defined amounts by weight of the components a) (meth)acrylate polymers, which may have quaternary ammonium groups, b) and organic di- or tricarboxylic acid and c) a plasticizer, which can be a citric acid triester.

As the above list shows, many plaster constructions and materials used for these are known. Similarly, today there is still a great demand for many active ingredients that are incorporated into Transdermal Therapeutic Systems to have a TTS available, which makes it possible to provide the therapeutically required release of the active ingredient, without the construction being expensive and in which, overall, the components are in an optimal relationship. This applies to the active ingredient, oxybutynin, when it is to be administered transcutaneously.

Therapeutically, oxybutynin is used for the symptomatic treatment of the hyperactivity of the detrusor (overactivity of the bladder muscle) with frequent urge to urinate, increased urination during the night, urgent urination, involuntary urination with or without the urge to urinate (incontinence). Transcutaneous application of oxybutynin with a TTS is desirable, since, by bypassing the gastrointestinal tract, and the first pass through the liver, concentration peaks of oxybutynin in the blood are avoided, which can lead to the occurrence of undesirable effects, such as dry mouth, accommodation disturbances, nausea and dizziness. Bypassing the first-pass metabolism in the liver can increase the bioavailability of oxybutynin in comparison to peroral administration, and the total dose can be reduced, which are necessary for reaching desired therapeutic effect.

Therefore, the task of the invention is to avoid the disadvantages of TTS with oxybutynin described above and to provide a TTS for transcutaneous administration of oxybutynin with good adhesive properties, which is simple to construct, is compatible with the skin and is physically and chemically stable over a long duration of storage and application, and a) releases on and through the skin as much active ingredient as possible per unit area, b) contains no skin penetration enhancer d) is free from solvent and d) in which the active ingredient oxybutynin undergo as little thermal exposure as possible.

In order to solve this task, a TTS and a method for its manufacture without the use of solvents is made available, the special composition of which can surprisingly fulfill the tasks described above. It contains and oxybutynin-containing matrix mass in the form of a layer which is self-adhesive, and in which the matrix mass consists of ammonium-group-containing (meth)acrylate copolymers, at least one citric acid triester and 5–25% by weight of oxybutynin. The TTs can be applied on the skin for several days.

Thus, because of its special composition, the addition of penetration enhancers is not necessary in the case of the TTS according to the invention.

In the sense of the invention the following terms and/or words are defined as given below:

a) "solvent-free": No solvent is used for the manufacture of the polymer matrices which solvent would have to be removed again largely during the manufacturing process, as it is done in the "solvent-based" method.

b) "several days": The TTS can be applied to the skin for therapeutic application for 1 to 7 days, preferably 1–4 days.

c) "short-term thermal exposure of the active ingredient" The active ingredient is added in the solid form to the polymer matrix heated to 150° C., is cooled to below its melting point within one minute.

d) "solid solution": The pharmaceutically active ingredient is present in the polymer/citric acid triester mixture in the molecularly dispersed form.

According to another embodiment according to the invention, the TTS described above can be surrounded additionally with the exception of the release surface of its oxybutynin-containing matrix on the skin by a larger but active-ingredient-free skin plaster for attachment at the application site (overtape).

This construction has the advantage that different skin types and climatic zones can be taken into consideration. Furthermore, the cohesion/adhesion properties of the TTS and the solubility of the active ingredient, rate of dissolution of the active ingredient and the release behavior can be optimized largely separately from one another.

According to a further development, the matrix mass preferably contains 10–20 weight % of oxybutynin.

Finally, the oxybutynin-containing matrix mass can be a solid solution.

The formation of a solid solution of oxybutynin in the ammonium-group-containing (meth)acrylate polymer was not predictable and it is especially surprising because many active ingredients do not form solid solutions in polymers (with a molecularly dispersed distribution), but are embedded into the particular polymer in the form of solid particles, which can be recognized with an electron microscope. In contrast to solid solutions, crystalline active ingredients also show a Debye-Scherrer diagram.

According to another embodiment of the invention, the oxybutynin-containing matrix mass preferably contains citric acid tributyl ester.

Finally, the oxybutynin-containing matrix mass may contain a mixture of citric acid butyl ester and citric acid triethyl ester.

Based on the composition according to the invention, and the structure of the TTS, it is surprising that, in spite of high active ingredient concentrations of oxybutynin in the polymer matrix, the system has sufficient physical stability upon long-term storage.

For the polymer used as active-ingredient-containing polymer matrix, it was not expected that directly after attaching the TTS there will be an intimate contact between the active ingredient matrix and the skin, which is of such quality that self-sufficient adhering TTS results over several days, which satisfies the therapeutic, industrial as well as operational economical requirements.

Thus the patient compliance is taken into consideration outstandingly.

If one chooses the embodiment with an active-ingredient-free skin plaster/overtape, a very small area skin plaster with an adhesive edge of only a few mm in width is required.

This is both economical as well as advantageous with regard to patient compliance.

According to another embodiment of the invention, the carrier film of the TTS has a metal vapor or oxide layer on the matrix side.

The TTS according to the invention can be produced according to the method described below.

A coatable oxybutynin-containing matrix mass is produced by melt extrusion in which the active component is metered continuously as a solid substance into a 150° C. polymer melt consisting of ammonium-group-containing (meth)acrylate copolymer and a citric acid triester so that a polymer melt with a content of up to 25 weight % of oxybutynin and up to 33 weight % of citric acid triester is obtained and the hot active-ingredient-containing polymer melt is coated immediately after the dosage of the active ingredient onto a separable protective layer (=substrate, carrier) to a thickness of 0.02 to 0.4 mm and the obtained 2-layer laminate is provided with a cover layer on the other side of the matrix.

The TTS provided with an additional skin plaster or overtape is produced as described below.

A coatable, oxybutynin-containing matrix mass is produced by melt extrusion, with the active ingredient being metered continuously into a polymer melt heated up to 150° C. and consisting of ammonium-group-containing (meth)acrylate copolymers and citric acid triester, so that a polymer melt with a content of up to 25 weight % of oxybutynin and up to 33 weight % of citric acid triester is obtained and the hot, active-ingredient-containing polymer melt is coated continuously immediately after the addition of the active ingredient onto a separable protective layer (=substrate, carrier) to a thickness of 0.02 to 0.4 mm and the obtained 2-layer laminate is provided with a cover layer on the other side of the matrix and then a larger active-ingredient-free plaster is applied for attachment of the TTS onto the skin.

The essential advantage of the method according to the invention, in contrast to the so-called "batch method" in which the weighed total amount of starting materials necessary for the production of a batch is used and their further processing to the pharmaceutical product is done in successive separate production steps, consists in the fact that the polymer matrix (I) which contains the active ingredient, is prepared without the use of organic solvents and (II) and that the preparation of the active-ingredient-containing matrix mass and its further processing to an active-ingredient-containing layer is done in one continuous and cost-saving process step: The process times can be shortened to a few minutes. The danger of decomposition reactions in the active-ingredient-containing polymer melt can be excluded in this way. Thus, furthermore, the active ingredient corresponds to the quality criteria of the DAB and/or of the European or US Pharmacopoeia. It was found surprisingly that complete dissolution and uniform distribution of the oxybutynin in the polymer melt is ensured in spite of the short processing times, under the processing conditions explained in more detail in the examples.

Furthermore, as a result of the continuous manufacture of the oxybutynin-containing polymer mass, when transferring the manufacturing process from laboratory to production scale, problems (scaling-up problems) are avoided, that is, when increasing the batch size, the manufacture of the active-ingredient-containing polymer melt and of the laminate does not require changing to a larger production installation, which usually involves qualification and validation work as well as optionally change in the formulation, which requires high cost and time expenditure.

BRIEF DESCRIPTION OF THE DRAWINGS

The structure of the TTS according to the invention is shown in drawings 1 and 2.

Drawing 1 shows the embodiment without overtape, consisting of active-ingredient-containing polymer matrix (1), separable protective film (5) and cover film (2).

Figure 1:
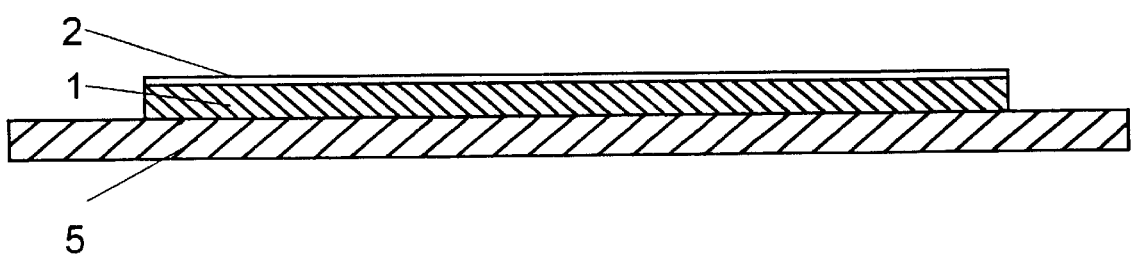
Figure 2:
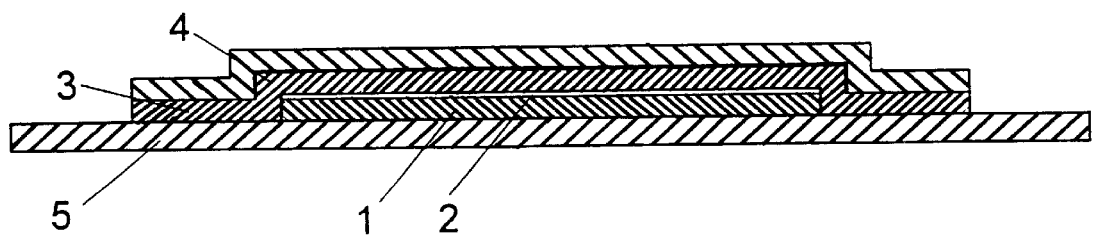

Drawing 2 shows the embodiment with overtape. In addition to the layers contained in the embodiment shown in drawing 1, an overtape consisting of carrier film (4) and adhesive film (3) are contained.

The invention will be explained with the aid of the following examples:

EXAMPLE 1

A two-screw extruder equipped with three dosage units is charged continuously in successive process zones with Eudragit RS 100 (copolymer of ethyl acrylate and methyl methacrylate with approximately 5% trimethylammonium-ethylmethacrylate chloride), tributyl citrate and oxybutynin, and the mixture is melt-extruded with a total throughput of 5 kg/h at a temperature of 110–140° C. From dosage unit 1, Eudragit RS 100 is introduced at a rate of 2.76 kg/h to the process part of the extruder, from dosing station 2 tributyl citrate is introduced at the rate of 1.49 kg/h and, finally, from dosage unit 3, oxybutynin is introduced at the rate of 0.75 kg/h. When leaving the extruder, the obtained hot oxybutynin-containing polymer melt is introduced through a heated inlet tubing directly in a continuous stream to the application head of the coating installation, and, a slit nozzle is applied onto an approximately 100 $\mu$m thick siliconized polyester film (=protective film (5)) at a thickness of approximately 100 g per m² (see drawing 1). After going through a roll-cooling device, the two-layer laminate is covered with an approximately 20 $\mu$m thick polyester film (cover film (2)). From the obtained web-shaped three-layer laminate, 12 cm² pieces are stamped out.

EXAMPLE 2

A two-screw extruder equipped with three dosage units is charged continuously in successive process zones with Eudragit RS 100 (copolymer of ethyl acrylate and methyl methacrylate with approximately 5% trimethylammonium-ethylmethacrylate chloride), tributyl citrate and oxybutynin, and the mixture is melt-extruded at a total throughput of 5 kg/h at a temperature of 110–140° C. From dosage unit 1, Eudragit RS 100 is introduced to the process part of the extruder at a rate of 2.76 kg/h, from dosage station 2, tributyl citrate is introduced at the rate of 1.49 kg/h and, finally, from dosage unit 3, oxybutynin is introduced at the rate of 0.75 kg/h. After leaving the extruder, the obtained hot oxybutynin-containing polymer melt is introduced through a heated inlet tubing in a continuous stream directly to the application head of the coating installation and, with the aid of a slit nozzle, it is applied onto an approximately 100 $\mu$m thick siliconized polyester film (=protective film (5)) at a thickness of approximately 100 g per m² (see drawing 2). After going through a roll-cooling installation, the two-layer laminate is covered with an approximately 20 $\mu$m thick polyester film (covering film=(inner) carrier film (2)).

From the obtained web-shaped three-layer laminate, the contours of 12 cm² matrix pieces were stamped out, and when doing this, the cover film (2) and the active-ingredient-containing polymer matrix (1) were cut through, but not the protective film (5). The obtained intermediate webs are separated by a lattice. On the obtained web-shaped laminate with format-stamped TTS matrices, a two-layer self-adhesive overtape film consisting of an approximately 80 qm [sic] thick adhesive film (3) based on a crosslinked acrylate copolymer and an (outer) carrier film (4) made of polyurethane are laminated. The resulting laminate is stamped to 20 cm² plasters consisting of components (1), (2), (3), (4), (5) according to drawing 2.

The two-screw extruder used in Examples 1 and 2 has defined length and has spatially separated feed devices along the longitudinal axis of the extruder for the substances to be used, called dosage unit or dosing station. Furthermore, the two-screw extruder can be divided along its length into process zones which can fulfill different purposes. For example, process zone may have a different thermal setting in relation to another.

Flux Measurements of Oxybutynin in vitro a) Flux Measurements Through Mouse Skin A TTS with a stamped area of 2.5 cm² is fixed in a horizontal diffusion cell on the horny layer side of the stomach and back skin of hairless mice. Directly afterward, the acceptor chamber of the cell is filled with a phosphate buffer solution having pH 6.2 (Ph. Eur., pH 6.4 R; adjusted to pH 6.2 with phosphoric acid), with its temperature controlled at 32° C. so that there are no air bubbles and the release medium is thermostated to 32±0.5° C.

At the sampling times (after 3, 6, 24, 30, 48, 54 and 72 hours) the release medium is replaced by fresh medium thermostated 32±0.5° C.

b) Flux Measurements Through Human Skin

The test was carried out according to Tiemessen (Harry L. G. M. Thiemessen et al. [Translator's note: There is a difference in spelling of name.], Acta Pharm. Technol. 24 (1998), 99–101). According to this described method, the flux measurement was carried out in a flow-through cell on freshly prepared, approximately 200 $\mu$m thick human skin, which was placed on a silicone membrane with its acceptor side (acceptor medium: phosphate buffer solution pH 6.2; thermostated to 32±0.5° C).

The samplings were done after 3, 6, 9, 12, 15, 21, 24, 27, 30, 36, 42, 48, 54, 60, 66 and 72 hours.

The oxybutynin content in the release and acceptor medium of the described model is determined with the aid of high-performance liquid chromatography (stationary phase: Cupelcosil LC-8-DB, 150 mm×4.6 mm, 3 μm; 45° C.; eluent: 29 parts by volume of acetonitrile and 71 parts by volume of a solution of 8 g of triethanolamine in 1000 mL of demineralized water, adjusted to pH 3.5 with phosphoric acid; UV detection at 200 nm; flow rate: 2.0 mL/minute; injection volume: 25 μL).

The results of the investigations are shown in Table 1 for Examples 1 and 2. The comparison with the flux rates known from the state of the art (see WO 95/09007 A1) in EVA-based polymer matrix systems shows that the oxybutynin is liberated from the TTS according to Examples 1 and 2 according to the invention in the "steady-state" at rates which are in the upper range or above of those in the state of the art. This is surprising since the flux rates of EVA-based polymer matrix systems known from the state of the art can only be achieved by having special additives present which enhance the penetration of oxybutynin through human skin in comparison to saturated solutions.

Furthermore, as the results of Table 1 show, with the matrix systems according to the present invention, surprisingly, a mean skin permeation rate (flux) is achieved which is clearly above the saturation fluxes of oxybutynin from the low-viscous solution described in WO 93/23025 A1, produced without any skin penetration enhancer (substances which are supposed to increase the permeability of skin to oxybutynin). With an acceptor medium temperature-controlled to a temperature by 3° C. lower than described in the literature data, the flux measurement on the plasters according to the invention were carried out even under conditions which are clearly unfavorable for the penetration of the active ingredient. Furthermore, Table 1 shows that with the matrix systems according to Examples 1 and 2, over the investigation time period of 3 days, a high exhaustion of the amount of active ingredient contained in the polymeric carrier material is achieved.

mass comprising a solid solution of a copolymer of ethyl acrylate and methyl methacrylate containing about 5% trimethylammonium ethyl methacrylate chloride as the sole (meth)acrylate copolymer, at least one citric acid triester, and 5 to 25 weight % of oxybutynin that underwent minimum thermal exposure, wherein said matrix mass is free of a skin penetration enhancer.

2. A transdermal therapeutic system for a transcutaneous administration of oxybutynin over one to four days at an application site on skin having an attachment aid for the system onto the skin, wherein the system comprises a self-adhesive layer-form oxybutynin-containing matrix mass, which comprises a solid solution of a copolymer of ethyl acrylate and methyl methacrylate containing about 5% trimethylammonium ethyl methacrylate chloride as the sole (meth)acrylate copolymer, at least one citric acid triester, and 5 to 25 weight % of oxybutynin that underwent minimum thermal exposure, wherein said matrix mass is free of a skin penetration enhancer and said mass is surrounded by a larger, oxybutynin-free plaster for attachment onto the skin, with the exception of a release surface at the application site.

3. The system according to claim 1 wherein the oxybutynin-containing matrix mass contains citric acid tributyl ester.

4. The system according to claim 1 wherein the oxybutynin-containing matrix mass contains citric acid tributyl ester in a mixture with citric acid triethyl ester.

5. The system according to claim 1 wherein the system further comprises a carrier having a metal vapor or oxide coating on a surface that contacts the matrix mass.

6. A method for the preparation of a transdermal therapeutic system for a transcutaneous administration of oxybutynin, wherein the oxybutynin is dosed continuously as a solid substance into a polymer melt heated up to 150° C., said polymer melt comprising (a) a copolymer of ethyl acrylate and methyl methacrylate containing about 5% trimethylammonium ethyl methacrylate chloride as the sole (meth)acrylate copolymer, and (b) a citric acid triester, such that a polymer melt having an oxybutynin content of 5 to 25

TABLE 1

Oxybutynin flux rates through excised skin preparations (Examples 1 and 2)

| | oxybutynin content of matrix or donor (weight %) | steady-state flux rate (μg/cm²/h) | mean cumulative flux mg/12 cm² | | |
|---|---|---|---|---|---|
| | | | after 24 h | after 48 h | after 72 h |
| Example 1: mouse skin n = 3 | 15 (18 mg/12 cm²) | 9.8 | 3.2 (17.5)* | 5.8 (32.3)* | 8.1 (45.0)* |
| Example 1: human skin (Thiemessen model) n = 4 | 15 (18 mg/12 cm²) | 8.9 | 1.6 (8.9)* | 4.2 (23.5)* | 6.7 (37.1)* |
| literature data** | | | | | |
| (1) WO 95/09007 A1 | 25 | range from approximately 4 to 10 | | | |
| (2) WO 93/23025 A1: oxybutynin solutions without special penetration enhancer | saturated solutions | range fnom approximately 2.5 to 4 | | | |

*) = cumulative flux in weight %, based on the active ingredient content of the matrix (100% = 18 mg)
**) = tests on excised human skin; receptor medium 0.05 M phosphate buffer; pH 6.5; 35° C.

What is claimed is:

1. A transdermal therapeutic system for a transcutaneous administration of oxybutynin over one to four days at an application site on skin, wherein the system comprises a self-adhesive layer-form oxybutynin-containing matrix weight %, a citric acid triester content of up to 33 weight %, and free of a skin penetration enhancer is obtained, then coating the oxybutynin-containing polymer melt after dosing of the oxybutynin onto a surface of a carrier at a thickness of 0.02 to 0.4 mm to provide a laminate, wherein the polymer melt is cooled to its melting point within one minute after oxybutynin dosing to maintain the oxybutynin in a nonmolten form, then applying a covering layer to the laminate on a surface of the carrier opposite the oxybutynin-containing polymer melt.

7. The method according to claim 6, wherein the polymer melt heated to 150° C. and continuously dosed with oxybutynin as a solid substance is coated continuously, after the dosage, onto a carrier, to a thickness of 0.02 to 0.4 mm, and the resulting 2-layer laminate is provided with a cover layer, then a larger, oxybutynin-free plaster is applied over the cover layer to attach the system onto skin.

8. A system according to claim 2 wherein the oxybutynin-containing matrix mass contains citric acid tributyl ester.

9. A system according to claim 2 wherein the oxybutynin-containing matrix mass contains citric acid tributyl ester in a mixture with citric acid triethyl ester.

10. A system according to claim 2 wherein the system further comprises a carrier having a metal vapor or oxide coating on a surface that contacts the matrix mass.

11. A method of producing a transdermal therapeutic system of claim 1 comprising:
(a) providing an extruder having a first inlet port for introducing the copolymer of ethyl acrylate and methyl methacrylate containing about 5% trimethylammonium ethyl methacrylate chloride, a second inlet port for introducing the citric acid triester, and a third inlet port for introducing the oxybutynin;
(b) continuously coextruding the ethyl acrylate and methyl methacrylate copolymer, citric acid triester, and oxybutynin at 110° C. to 140° C. as a laminate matrix mass of thickness 0.02 to 0.4 mm onto a protective film, and cooling the laminate matrix mass to the melting point of the ethyl acrylate and methyl methacrylate copolymer within one minute to maintain the oxybutynin in a nonmolten form; and
(c) applying a cover film on a surface of the laminate matrix mass opposite from the protective film.

12. A transdermal therapeutic system for transcutaneous administration of oxybutynin over one to four days at an application site on skin having an attachment aid for the system onto the skin, wherein the system comprises a self-adhesive layer-form oxybutynin-containing matrix mass disposed on a protective film, and said matrix mass consisting essentially of a solid solution of (a) a copolymer of ethyl acrylate and methyl methacrylate containing about 5% trimethylammonium ethyl methacrylate chloride as the sole (meth)acrylate copolymer, (b) at least one citric acid triester, and (c) about 5 to about 25 weight percent of oxybutynin distributed in a molecularly dispersed form in the matrix mass, and surrounded by a larger oxybutynin-free plaster for attachment to the skin, with the exception of a release surface on the skin, wherein said system is prepared by a method comprising:
(a) providing an extruder having a first inlet port for introducing the copolymer of ethyl acrylate and methyl methacrylate containing about 5% trimethylammonium ethyl methacrylate chloride, a second inlet port for introducing the citric acid triester, and a third inlet port for introducing the oxybutynin;
(b) continuously coextruding the ethyl acrylate and methyl methacrylate copolymer, citric acid triester, and oxybutynin at 110° C. to 140° C. as a laminate matrix mass of thickness 0.02 to 0.4 mm onto a protective film, and cooling the laminate matrix mass to the melting point of the ethyl acrylate and methyl methacrylate copolymer within one minute to maintain the oxybutynin in a nonmolten form; and
(c) applying a cover film on a surface of the laminate matrix mass opposite from the protective film.

* * * * *

UNITED STATES PATENT AND TRADEMARK OFFICE
CERTIFICATE OF CORRECTION

PATENT NO.      : 6,555,129 B1
DATED           : May 29, 2003
INVENTOR(S)     : Christoph Arth et al.

It is certified that error appears in the above-identified patent and that said Letters Patent is hereby corrected as shown below:

<u>Column 5,</u>
Line 24, "contains and" should be -- contains an --
Line 29, "TTs" should be -- TTS --

Signed and Sealed this

Fourteenth Day of October, 2003

JAMES E. ROGAN
*Director of the United States Patent and Trademark Office*